United States Patent [19]

Uematsu et al.

[11] Patent Number: 4,629,744
[45] Date of Patent: Dec. 16, 1986

[54] METHOD FOR PRODUCING A RESPONSE MEMBRANE FOR USE IN A CHLORIDE ION SELECTIVE ELECTRODE

[75] Inventors: Hiroaki Uematsu; Takeshi Kohno; Takeshi Miyazaki, all of Kyoto, Japan

[73] Assignee: Horibe, Ltd., Kyoto, Japan

[21] Appl. No.: 714,082

[22] Filed: Mar. 20, 1985

[30] Foreign Application Priority Data

Mar. 23, 1984 [JP] Japan .................. 59-56778

[51] Int. Cl.$^4$ .............................. C08J 9/28
[52] U.S. Cl. ........................ 521/62; 521/63; 521/64; 521/94; 521/135; 428/220; 525/113; 525/121
[58] Field of Search ............. 525/113, 121; 521/62, 521/63, 135, 64, 94; 428/220

[56] References Cited

U.S. PATENT DOCUMENTS

| | | |
|---|---|---|
| 3,278,477 | 10/1966 | Evans .................................... 525/113 |
| 3,347,951 | 10/1967 | Vasta .................................... 525/113 |
| 3,948,823 | 4/1976 | Lee et al. ............................. 521/62 |

FOREIGN PATENT DOCUMENTS

| | | | |
|---|---|---|---|
| 745060 | 2/1966 | United Kingdom ............... 525/113 |
| 1104274 | 2/1968 | United Kingdom ............... 525/113 |
| 1169857 | 11/1969 | United Kingdom ............... 525/113 |

Primary Examiner—John C. Bleutge
Assistant Examiner—Robert E. L. Sellers, II
Attorney, Agent, or Firm—Wenderoth, Lind & Ponack

[57] ABSTRACT

A composition for use in a chloride ion electrode is provided herein. This composition is made up of a mixture of an epoxy resin, a vinyl chloride resin, one or more solvents, a quaternary ammonium salt and hardening agents for setting said epoxy resin; wherein said epoxy resin and the vinyl chloride resin is used at a ratio of 8:1 to 1:2 by weight. The present invention also relates to a response membrane produced from said composition and a method for producing the response membrane by setting or hardening the aforementioned composition. When the response membrane is used in the chloride ion selective electrode, it is capable of measuring a sample containing blood or protein and by use of the response membrane, it is possible to selectively determine chloride ions in a sample with a high degree of accuracy.

11 Claims, 6 Drawing Figures

METHOD FOR PRODUCING A RESPONSE MEMBRANE FOR USE IN A CHLORIDE ION SELECTIVE ELECTRODE

BACKGROUND OF THE INVENTION

1. Field of the Invention

The present invention primarily relates to a response membrane for use in a chloride ion selective electrode for measuring a sample containing blood or protein. It is an object of the present invention to provide a response membrane capable of containing a stable reading or measurement of (Cl$^-$) without drifting during the measurement and without being subjected to interferences by other ions. Further, by use of the response membrane of the present invention, it is possible to measure chlorine ions with a high degree of accuracy and the response membrane is superior in linearity to other known membranes.

2. Description of the Prior Art

There have been known the following three types of methods for producing a response membrane for use in a chloride ion selective electrode:

(a) A method for forming a response membrane made of a solid molded membrane chiefly comprising silver chloride;

(b) A method for producing a response membrane by enclosing a responsive substance and a solvent in a plastic membrane made of vinyl chloride; and (c) A method for producing a response membrane by holding a responsive subject dissolved in a suitable organic solvent in a porous membrane.

However, when a response membrane produced according to the method (a) is used, both the phenomenon of drift and hunching are increased if the measurement is carried out on blood without diluting it, thereby giving rise to inaccurate measurements. At this time, if the response membrane is once influenced by the interference of a protein, the indication or reading does not return to the original reading, even if the interfering ions are eliminated. In addition, a response membrane of this type has such a disadvantage that the influence by a protein and the like cannot be removed even though the surface of the response membrane is coated with a hydrophobic polymer, such as DURAGUARD and the DURAGUARD coat must be exchanged once every two weeks.

When a response membrane produced according to the method (b) is used, the chloride ion selective electrode has such a disadvantage that it is inferior in linearity, the drift in the serum is increased, and the span of life of the electrode is remarkably shortened to about two weeks.

A liquid membrane type electrode produced according to method (c) has such disadvantages in that the span of life is shortened since the sample is contaminated with the organic layer, and the electrode is complicated in construction, even though the porous membrane is made to be exchangeable, and it requires maintenance, which is time consuming. This type of electrode also has such disadvantages that it is inferior in mechanical strength, and is particularly weak against vibration.

SUMMARY OF THE INVENTION

It is an object of the present invention to provide a response membrane capable of eliminating the above-described disadvantages of the methods (a) to (c) and a method for producing the same.

In order to achieve this object, in the present invention, a mixture consisting of a blend of an epoxy resin and a vinyl chloride resin at a ratio of 8:1 to 1:2 by weight, solvents, quaternary ammonium salts and hardening agents for setting the eposy resin, which is set or hardened by holding it at temperatures of 35° to 45° C. for 20 days or more.

DETAILED DESCRIPTION OF THE INVENTION

The various ingredients used for preparing the response membrane of the present invention and the preferred proportions thereof are as follows:

(a) A bisphenol type, which belongs to a methyl-substituted bisphenol resin, is preferably used for the epoxy resin.

(b) A vinyl chloride resin having a polymerization degree of 1,100 to 2,800 is preferably used.

The epoxy resin and the vinyl chloride resin are used at a ratio of 8:1 to 1:2 by weight. If the proportions of these resins do not fall within this ratio, certain disadvantages occur; thus, where ⅛ part or less of the vinyl chloride is mixed with 1 part of the epoxy resin, the internal resistance increases exponentaially by 1 (to be 110$^8$ ohms or more), while if more than 2 parts of the vinyl chloride are mixed with 1 part of the epoxy resin, the drift in the serum is suddenly increased.

(d) The epoxy resin is preferably used at a ratio of 30 to 50% by weight, based on the whole composition. Where the epoxy resin is used at a ratio of 30% by weight or less, the drift in serum is increased, even if the hardening agents are used in a larger quantity, but where the epoxy resin is used at a ratio of 50% by weight or more, the internal resistance is increased and the span of life of the electrode in the standard solution is shortened.

(e) Amines, in particular aliphatic polyamines, are preferably used as hardening agents. The differences in the drift in the serum, as measured by the shift in potential, depends on the hardening agents as shown in FIG. 1. Referring to FIG. 1, a shows the curve in the case where triethylene tetramine (TETA), which is most popular among aliphatic polyamines, is used as the hardening agent and b shows the curve in the case where a lacquer amide (a diethylene triamine adduct), which is one of the denatured aliphatic polyamines, is used as a hardening agent.

(f) The hardening agents are preferably used at a ratio of 40 to 60 parts by weight, based on 100 parts by weight of the epoxy resin. When the hardening agents are used at a ratio of 40 parts by weight or less, the drift in serum is increased regardless of the quantity of the epoxy resin.

(g) Dialkylphthalate or phenylalkyl alcohol and alkylnitrophenyl ether having high dielectric constants are preferably used as the solvents.

The difference in the drift in serum in the case where dialkylphthalate and dialkyladipate are used as the solvents and the epoxy resin is used in an amount of 10% by weight is shown in FIG. 2.

In addition, the differences in the drift of the serum as a function of the solvents used are shown in FIG. 3, in cases where the epoxy resin is used in an amount of 35% by weight.

(h) The solvents are preferably used at a ratio of 3:7 to 2:1 by weight, based on the total amount of the epoxy resin and the vinyl chloride resin.

(i) As the responsive substances, quaternary ammonium salts, such as trioctylmethylammonium chloride (TOMA), tridecylmethylammonium chloride (TDMA) and tetraoctylmethylammcnium chloride are preferably used. The responsive substance is preferably used in an amount of 0.4 to 30% by weight based on the weight of the whole composition. In cases where it is used at a ratio of 0.4% by weight or less, the response becomes slower at low concentrations, whereas, when it is used in an amount of 30% by weight or more, the selection ratio of the electrode becomes inferior.

(j) The coat is preferably 0.2 to 0.3 mm thick. When the coat is adhered to the electrode with tetrahydrofuran containing vinyl chloride at a ratio of 0.2 to 2%, the coat is best adhered to the body of the electrode at the aforementioned thickness range. In addition, it was confirmed that there was no change in such performances as linearity and serum measurements when the coat was 0.1 to 0.7 mm thick.

DESCRIPTION OF THE PREFERRED EMBODIMENTS

The composition as shown in the following table is used in the production of a response membrane:

TABLE

| Epoxy resin | Bisphenol type epichlone 840 | 408 mg |
|---|---|---|
| Hardening agent | Triethyltetramine | 180 mg |
| Vinyl chloride resin (PVC) | Polymerization degree 2,500 | 120 mg |
| Quaternary ammonium salt | Trioctylammonium chloride | 60 mg |
| Solvent | Diamylphthalate | 420 mg |
| Volatile solvent | Tetrahydrofuran (THF) | 10 mg |

The response membrane of the present invention is produced according to the following procedure:

At first PVC is dissolved in THF by the use of an Erlenmeyer flask.

Then the solvents are added to said flask.

TOMA (trioctylammonium chloride) is then added to the above mixture.

The epoxy resin is then added.

A rotor (10 to 15 mm) is put in the Erlenmeyer flask containing the above mixture and the content is stirred for 30 minutes or more. Since epichlone is considerably viscous, if the content is insufficiently stirred, the epoxy resin partially forms lumps after the formation of the coat.

Hardening agents are then added and the mixture is stirred for about 30 minutes. It appears that the epoxy resin begins to set by the addition of the hardening agents to form a response membrane. The response membrane did not show any changes when stirred for 10 to 60 minutes.

The response membrane thus-produced is transferred into a shallow cylindrical vessel made of Teflon, covered with two pieces of filter paper and a glass plate and then purged with $N_2$ for 2 or 3 days in a desiccator. THF is completely volatilized within 3 days (in the winter).

Then, the response membrane is transferred into a shallow cylindrical vessel made of glass and preserved at a temperature of 40° C. ($\pm 5°$ C.) in a drier. At this time, attention must be paid not to place the membrane in the light (sun). The response membrane was preserved for 20 days or more. It was confirmed that the response membrane would be changed in color and hardness within 20 days, since it was still being hardened. In addition, in the case where the response membrane was preserved at a temperature of 40° C. for merely a short term of about 3 to 5 days, there was no problem in linearity, but a fluctuation of potential shift occurred in a serum measurement and the like. The response membrane preserved for 20 days or more did not show such a fluctuation of potential shift.

The response membrane is then taken out of the drier and preserved in a desiccator (room temperature). However, again attention must be paid not to place the membrane in the light (especially the sunlight).

Figure 1:
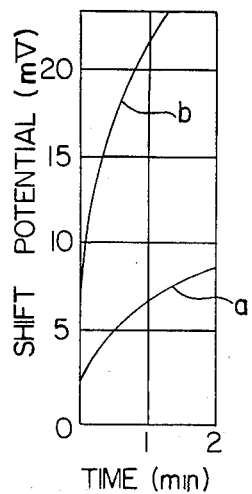
FIG. 1 is a graph showing the differences in the drift in a serum depending upon the hardening agents used.
Figure 2:
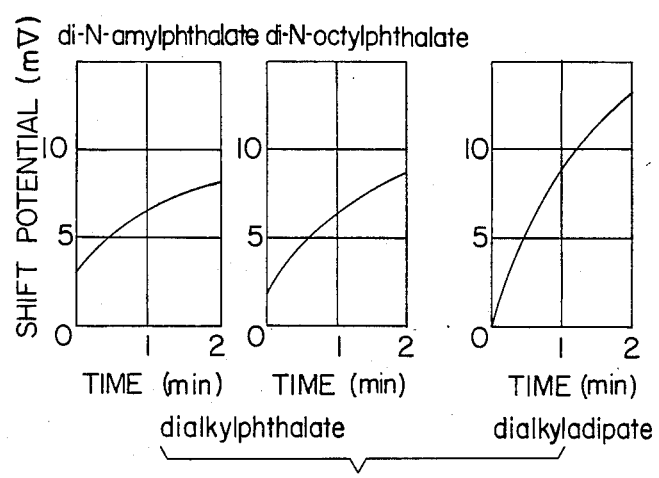
FIGS. 2 and 3 are graphs showing the differences in drift depending upon solvents employed.
Figure 3:
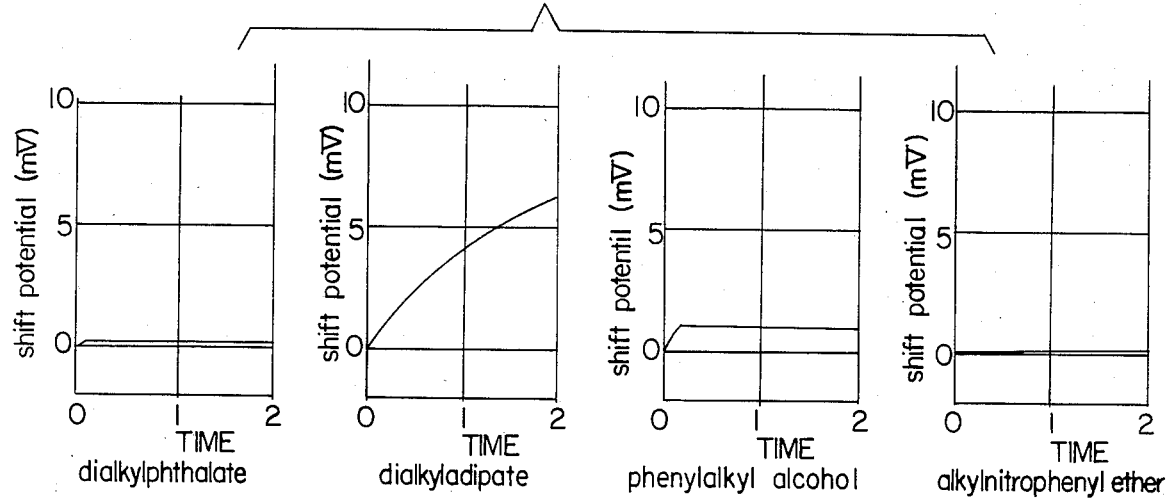
Figure 4:
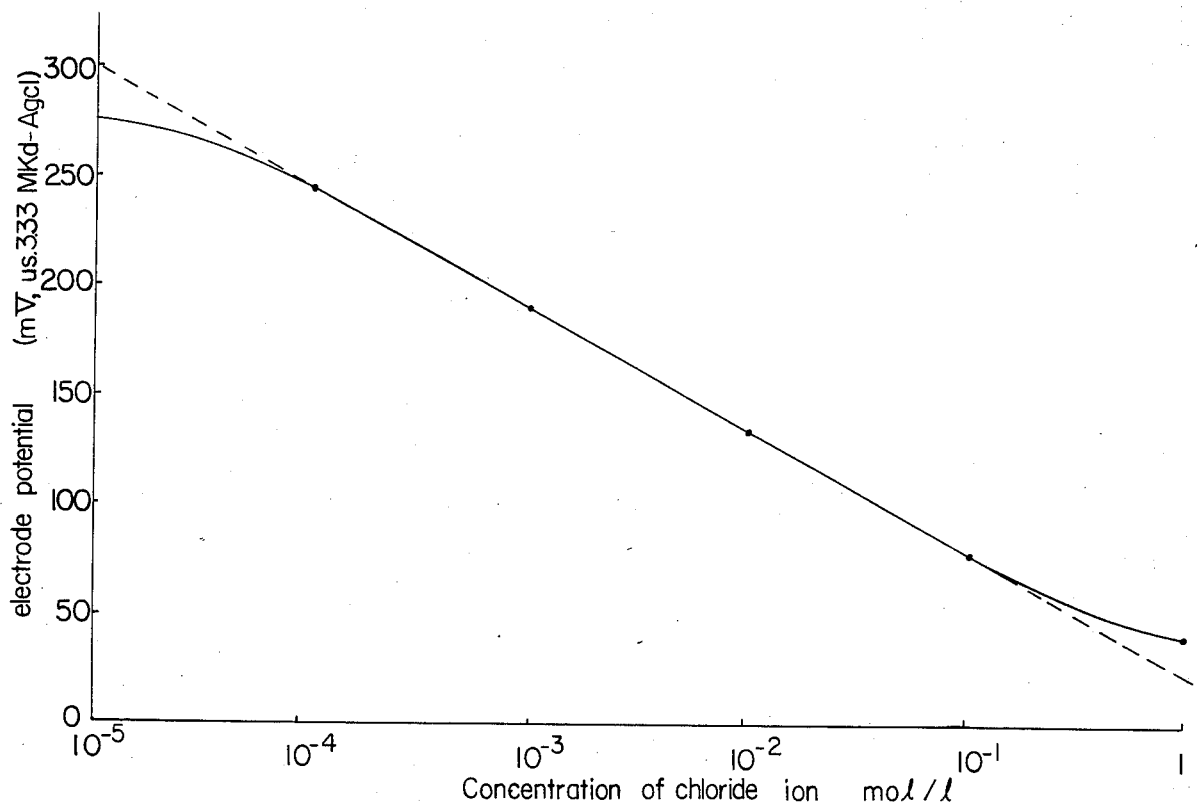
FIG. 4 is a graph showing the results of tests on the linearity of a $Cl^-$ electrode.

The performance test results of the response membrane produced in the above described manner will be enumerated below:

Linearity: as shown in FIG. 4, the response membrane responds to $Cl^-$ in amounts of 1 to $10^{-5}$ mol/liter and shows a superior linear range of $10^{-1}$ to $10^{-4}$ mol/liter.

Interference: The selection factors of the response membrane for other anions were examined in comparison with a known $NO^{-3}$ electrode. The results are shown in the following table:

| | (at $Cl^-$ $10^{-2}$ mol/liter) | |
|---|---|---|
| Coexisting ion | Response membrane produced according to a method of the present invention | Known response membrane |
| $Br^-$ | 3.1 | 5.9 |
| $I^-$ | 18.5 | 260 |
| $NO_3^-$ | 5.7 | 22 |
| $HCO_3^-$ | 0.08 | 0.21 |
| $CH_3COO^-$ | 0.24 | 0.34 |
| $SO_4^{2-}$ | 0.04 | 0.01 |

It is found from the above-described table that the selection ratios (e.g., in the instant case for chloride ions) of the ion electrode using the membrane produced according to the present invention is considerably superior to that of the known $NO_3^-$ electrode, in that interferences caused by other anions can be considerably suppressed. Here, the known response membrane is a response membrane for use in a $NO_3^-$ electrode produced according to the method disclosed in Japanese Patent Application Laid-Open No. 55747/1983.

Response speed: 99% of the response can be obtained within 30 seconds in a range of $10^{-1}$ to $10^{-2}$ mol/liter of $Cl^-$ by using electrodes containing the membrane of the present invention.

Reproductivity: the reproductivity was superior in every case over those of said known electrode in respect to the measurement of a standard solution, serum and whole blood.

Influence of pH: it was confirmed that the pH did not influence the performance of the membranes of the present invention in a pH range of 3 to 10.

Span of life: the response membrane of the present invention was stable for one year or more. Also, in the case of the serum measurement the span of life of Applicants' membrane was long, extending to 5 months or more. The response membrane tested was 0.25 mm thick.

Figure 5:
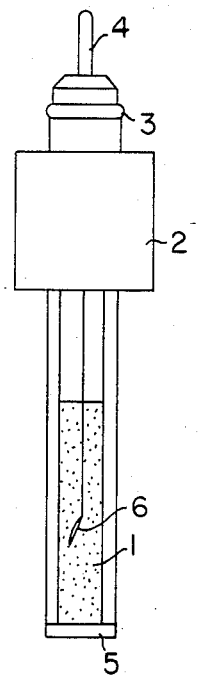
FIGS. 5 and 6 show electrodes in which the response membrane produced according to a method of the present invention is used.
Figure 6:
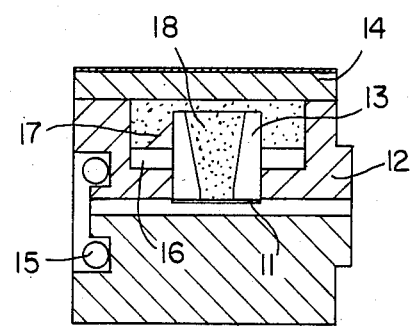

Next, the applications or uses of the above-described response membrane are shown in FIGS. 5 and 6. Referring to FIG. 5, a tip type electrode (immersion measurement type) is illustrated in which 1 is an internal solution, 2 is a body, 3 is an O-ring, 4 is a connector pin, 5 is a Cl$^-$ response membrane and 6 is an internal electrode (Ag/AgCl).

FIG. 6 illustrates a flow-through type electrode, wherein 11 is a Cl$^-$ response electrode, 12 is a cell, 13 is a ring, 14 is a cover, 15 is an O-ring, 16 is a filler (silicon resin), 17 is an internal electrode, and 18 is an internal solution.

As described above, the present invention is capable of producing a response membrane, which is superior in linearity, is capable of obtaining a stable reading without showing any drifts, and is hardly influenced by other anions, thereby making it possible to selectively determine Cl$^-$ with a high degree of accuracy.

What is claimed is:

1. A method for producing a response membrane for use in a chloride ion selective electrode comprising preparing a mixture of an epoxy resin, a vinyl chloride resin, one or more solvents, 0.4 to 30% by weight of a quaternary ammonium salt, based upon the weight of the mixture, as a responsive substance for detecting chloride ions, and a hardening agent for setting said epoxy resin, wherein said epoxy resin and said vinyl chloride resin is used at a ratio of 8:1 to 1:2 by weight, placing the mixture in a shallow vessel and evaporating the solvents to form a membrane, and hardening the membrane by maintaining it at a temperature of 45° C. for 20 days or more to produce the response membrane.

2. A method for producing a response membrane according to claim 1, wherein said hardening agent is an aliphatic polyamine.

3. A method for producing a response membrane for use in a chloride ion selective electrode as set forth in claim 1, wherein said epoxy resin is used in an amount of 30 to 50% by weight, based on the weight of the whole composition.

4. A method for producing a response membrane for use in a chloride ion selective electrode as set forth in claim 1, wherein said hardening agent is used in an amount of 40 to 60 parts by weight based on 100 parts by weight of said epoxy resin.

5. A response membrane produced according to the method of claim 1.

6. A method according to claim 1, wherein the quaternary amonium salt is a quaternary ammonium chloride.

7. A method according to claim 6, wherein the quaternary ammonium chloride is selected from the group consisting of trictylmethylammonium chloride, tridecylmethylammonium chloride and tetraoctylmethylammonium chloride.

8. A method according to claim 1, wherein the membrane is 0.1 to 0.7 mm thick.

9. A method according to claim 8, wherein the membrane is 0.2 to 0.3 mm thick.

10. A method according to claim 1, wherein the membrane is protected from light during the hardening period.

11. A method according to claim 1, wherein the solvents are employed in a ratio of 3:7 to 2:1 by weight, based on the total amount of the epoxy resin and the vinyl chloride resin.

* * * * *